United States Patent [19]
Yoon

[11] Patent Number: 5,957,937
[45] Date of Patent: *Sep. 28, 1999

[54] SUTURING INSTRUMENT WITH SPREADABLE NEEDLE HOLDER MOUNTED FOR ARCUATE MOVEMENT

[76] Inventor: InBae Yoon, 2101 Highland Ridge Dr., Phoenix, Md. 21131

[ * ] Notice: This patent issued on a continued prosecution application filed under 37 CFR 1.53(d), and is subject to the twenty year patent term provisions of 35 U.S.C. 154(a)(2).

[21] Appl. No.: 08/904,767

[22] Filed: Aug. 1, 1997

Related U.S. Application Data

[63] Continuation-in-part of application No. 08/758,648, Nov. 27, 1996, Pat. No. 5,759,188, application No. 08/847,182, May 1, 1997, and application No. 08/877,764, Jun. 17, 1997.

[51] Int. Cl.⁶ .................................................. A61B 17/04
[52] U.S. Cl. ......................... 606/147; 606/144; 606/145
[58] Field of Search ............................ 606/139, 144–148

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,131,163 | 3/1915 | Saunders et al. . |
| 1,155,378 | 10/1915 | Steedman . |
| 1,449,087 | 3/1923 | Bugbee . |
| 1,822,330 | 9/1931 | Ainslie . |
| 1,916,722 | 7/1933 | Ende . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes ................................... 606/144 |
| 4,164,225 | 8/1979 | Johnson et al. . |
| 4,257,420 | 3/1981 | Terayama ............................... 128/303 |
| 4,440,171 | 4/1984 | Nomoto et al. . |
| 4,557,265 | 12/1985 | Andersson . |
| 4,621,640 | 11/1986 | Mulhollan et al. . |
| 4,635,638 | 1/1987 | Weintraub et al. . |
| 4,935,027 | 6/1990 | Yoon . |
| 5,037,433 | 8/1991 | Wilk et al. ............................. 606/139 |
| 5,100,421 | 3/1992 | Christoudias . |
| 5,147,373 | 9/1992 | Ferzli . |
| 5,181,919 | 1/1993 | Bergman et al. . |
| 5,209,741 | 5/1993 | Spaeth . |
| 5,211,650 | 5/1993 | Noda ....................................... 606/139 |
| 5,222,508 | 6/1993 | Contarini ............................... 128/898 |
| 5,234,443 | 8/1993 | Phan et al. ............................. 606/148 |
| 5,244,948 | 9/1993 | Mulhaupt et al. . |

(List continued on next page.)

FOREIGN PATENT DOCUMENTS

WO 97/37583   10/1997   WIPO .

*Primary Examiner*—Gary Jackson
*Attorney, Agent, or Firm*—Blank Rome Comisky & McCauley LLP

[57] ABSTRACT

An instrument for suturing anatomical tissue with a suture needle includes a housing, an elongate tubular member mounted by the housing, and a needle holder having a distal end movable between an undeployed position disposed laterally inward of a peripheral edge of the elongate tubular member and a deployed position disposed laterally outward of the peripheral edge. The needle holder is coupled with the housing for arcuate movement about a longitudinal axis of the elongate tubular member such that a corresponding distal end of the needle holder is caused to move along an arcuate path extending outwardly of the peripheral edge and having a radius of curvature commensurate with the radius of curvature of the suture needle.

21 Claims, 7 Drawing Sheets

U.S. PATENT DOCUMENTS

| | | | |
|---|---|---|---|
| 5,261,917 | 11/1993 | Hasson et al. | 606/139 |
| 5,281,238 | 1/1994 | Chin et al. . | |
| 5,304,185 | 4/1994 | Taylor | 606/147 |
| 5,305,121 | 4/1994 | Moll . | |
| 5,308,353 | 5/1994 | Beurrier | 606/144 |
| 5,320,632 | 6/1994 | Heidmueller | 606/144 |
| 5,336,230 | 8/1994 | Leichtling et al. . | |
| 5,336,231 | 8/1994 | Adair | 606/148 |
| 5,356,424 | 10/1994 | Buzerak et al. . | |
| 5,364,408 | 11/1994 | Gordon . | |
| 5,364,409 | 11/1994 | Kuwabara et al. | 606/148 |
| 5,374,275 | 12/1994 | Bradley et al. . | |
| 5,376,096 | 12/1994 | Foster | 606/147 |
| 5,389,098 | 2/1995 | Tsuruta et al. . | |
| 5,389,103 | 2/1995 | Melzer et al. | 606/144 |
| 5,395,367 | 3/1995 | Wilk . | |
| 5,397,325 | 3/1995 | Della Badia et al. . | |
| 5,403,328 | 4/1995 | Shallman | 606/144 |
| 5,403,329 | 4/1995 | Hinchcliffe | 606/147 |
| 5,437,681 | 8/1995 | Maede et al. | 606/145 |
| 5,454,823 | 10/1995 | Richardson et al. . | |
| 5,462,561 | 10/1995 | Voda | 606/144 |
| 5,462,562 | 10/1995 | Elkus | 606/148 |
| 5,468,251 | 11/1995 | Buelna | 606/223 |
| 5,470,338 | 11/1995 | Whitfield et al. . | |
| 5,474,057 | 12/1995 | Makower et al. . | |
| 5,474,568 | 12/1995 | Scott | 606/144 |
| 5,477,794 | 12/1995 | Klundt . | |
| 5,478,344 | 12/1995 | Stone et al. . | |
| 5,478,345 | 12/1995 | Stone et al. . | |
| 5,480,406 | 1/1996 | Nolan et al. . | |
| 5,496,310 | 3/1996 | Exconde et al. . | |
| 5,496,334 | 3/1996 | Klundt et al. . | |
| 5,503,634 | 4/1996 | Christy | 606/144 |
| 5,520,703 | 5/1996 | Essig et al. . | |
| 5,540,704 | 7/1996 | Gordon et al. . | |
| 5,540,705 | 7/1996 | Maede et al. . | |
| 5,545,148 | 8/1996 | Wurster . | |
| 5,562,640 | 10/1996 | McCabe et al. . | |
| 5,562,685 | 10/1996 | Mollenauer et al. . | |
| 5,562,686 | 10/1996 | Sauer et al. . | |
| 5,562,703 | 10/1996 | Desai . | |
| 5,569,164 | 10/1996 | Lurz . | |
| 5,569,269 | 10/1996 | Hart et al. . | |
| 5,569,270 | 10/1996 | Weng . | |
| 5,573,542 | 11/1996 | Stevens . | |
| 5,578,048 | 11/1996 | Pasqualucci et al. . | |
| 5,582,617 | 12/1996 | Klieman et al. . | |
| 5,591,181 | 1/1997 | Stone et al. . | |
| 5,601,575 | 2/1997 | Measamer et al. | 606/147 |
| 5,603,718 | 2/1997 | Xu . | |
| 5,607,435 | 3/1997 | Sachdeva et al. | 606/139 |
| 5,609,601 | 3/1997 | Kolesa et al. . | |
| 5,626,588 | 5/1997 | Sauer et al. | 606/144 |
| 5,632,751 | 5/1997 | Piraka | 606/139 |
| 5,632,752 | 5/1997 | Buelna | 606/144 |
| 5,643,292 | 7/1997 | Hart | 606/144 |
| 5,662,663 | 9/1997 | Shallman | 606/144 |
| 5,674,230 | 10/1997 | Tovey et al. | 606/139 |
| 5,707,379 | 1/1998 | Fleenor et al. | 606/145 |
| 5,709,693 | 1/1998 | Taylor | 606/145 |
| 5,709,694 | 1/1998 | Greenberg et al. | 606/148 |
| 5,713,908 | 2/1998 | Jameel et al. . | |
| 5,722,990 | 3/1998 | Sugarbaker et al. . | |

SUTURING INSTRUMENT WITH SPREADABLE NEEDLE HOLDER MOUNTED FOR ARCUATE MOVEMENT

CROSS-REFERENCE TO RELATED APPLICATIONS

This application is a continuation-in-part of application Ser. No. 08/758,648, filed Nov. 27, 1996 U.S. Pat. No. 5,759,188, Ser. No. 08/847,182, filed May 1, 1997 still pending, and Ser. No. 08/877,764, filed Jun. 17, 1997 still pending, the disclosures of which are incorporated herein by reference.

BACKGROUND OF THE INVENTION

1. Field of the Invention

The present invention pertains to suturing of bodily or anatomical tissue and, more particularly, to an apparatus and method for suturing anatomical tissue during endoscopic and open surgical procedures.

2. Discussion of the Related Art

Suturing of bodily tissue, that is, the practice of using lengths of suture material to ligate or approximate tissue, is a time consuming part of most surgical procedures including both open surgery and endoscopic or closed surgery. By "open surgery" is meant surgery wherein the surgeon gains access to the surgical site by a relatively large incision and by "endoscopic surgery" is meant minimally invasive surgery wherein the surgeon gains access to the surgical site via one or more portals through which endoscopes are introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period in which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in open and endoscopic surgery to permit surgeons to suture anatomical tissue using suture needles and lengths of suture material in a time efficient, consistent and precise manner.

The performance of an endoscopic procedure typically involves creation of one or a number of puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity. Suturing is typically performed with a needle holding instrument or holder having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must either be opened to release the suture needle so that the tip of the needle can be grasped and pulled through the tissue therewith, or a second needle holding instrument must be introduced at the operative site through another portal to grasp the tip of the suture needle after it has emerged from the tissue being sutured. The former technique requires further adjustment of the suture needle within the jaws of the needle holder before another stitch can be made; and, while use of a second needle holding instrument for pulling the needle through the anatomical tissue allows the first needle holding instrument to grasp the body of the suture needle in the manner required to make additional stitches, it is generally desirable to minimize the number of puncture sites created for performing a particular endoscopic procedure.

SUMMARY OF THE INVENTION

Accordingly, it is a primary object of the present invention to overcome the above-mentioned disadvantages of the prior art and to improve suturing instruments and methods of suturing anatomical tissue.

Another object of the present invention is to permit suturing of anatomical tissue without the need of having to use multiple needle holding instruments.

Yet another object of the present invention is to minimize the number of puncture sites required for suturing anatomical tissue in an endoscopic procedure by inserting a needle holder through a single portal with a suturing instrument that is operable to move the needle holder to suture anatomical tissue.

An additional object of the present invention is to permit suturing of anatomical tissue in an endoscopic procedure using a curved suture needle having a radius of curvature larger than a radial dimension of the portal through which the suturing instrument is inserted.

It is a further object of the present invention to permit a suturing instrument as well as other medical instruments and devices to be introduced through a single portal in an endoscopic procedure without the need of having to withdraw the suturing instrument from the portal.

Some of the advantages of the present invention over the prior art are that suturing of anatomical tissue can be accomplished in a time efficient, consistent and precise manner, that suturing can be accomplished using standard suture needles and filamentous suture materials without the need of having to insert additional instruments at the operative site, that single-handed suturing is made possible, that conventional handle structures can be used to provide users with a familiar feel and to decrease adaptation time, and that the instrument can be made sterilizable for reuse or disposable for single patient use as desired.

The present invention is generally characterized in an instrument for suturing anatomical tissue with a suture needle including a housing, an elongate tubular member having a proximal end mounted by the housing and a distal end with a peripheral edge, and a needle holder having a distal end movable between an undeployed position where the distal end of the needle driver is disposed laterally inward of the peripheral edge of the elongate tubular member and a deployed position where the distal end of the needle driver is disposed laterally outward of the peripheral edge. The needle holder is coupled with the housing for arcuate movement about a longitudinal axis of the elongate tubular member such that a corresponding distal end of the needle holder is caused to move along an arcuate path having a radius of curvature greater than the distance between the longitudinal axis and the peripheral edge of the elongate tubular member. In addition, the distal end of the needle holder is operable to grasp and release a suture needle so that a suture needle having a radius of curvature commensurate with the radius of curvature of the arcuate path can be driven through tissue using the distal end of the needle holder and subsequently pulled through the tissue by repositioning the needle holder. An inner tubular member may be disposed within the elongate tubular member with a small radial clearance to define an annular space therebetween, with the needle holder being movably disposed within the annular space. If provided, the inner tubular member preferably extends through the housing to define a longitudinal operating passage or channel along the length of the instrument, with a valve and/or a coupling preferably being disposed at a proximal end of the operating channel to control passage of fluids and instruments through the channel.

Another aspect of the present invention is generally characterized in a method of suturing anatomical tissue using a length of suture material attached to a suture needle including the steps of grasping the suture needle with a needle holder extending laterally outward at an angle from a distal end of an elongate tubular member, driving the suture needle through the anatomical tissue by moving the needle holder in a first direction along an arcuate path having a radius of curvature substantially commensurate with the radius of curvature of the suture needle to cause the tip of the needle to penetrate the anatomical tissue, releasing the suture needle from the needle holder, repositioning the needle holder to receive the tip of the suture needle, regrasping the suture needle with the needle holder, and pulling the suture needle through the anatomical tissue by moving the needle holder in the first direction along an arcuate path having a radius of curvature substantially commensurate with the radius of curvature of the suture needle.

Other objects and advantages of the present invention will become apparent from the following description of the preferred embodiments taken in conjunction with the accompanying drawings, wherein like parts in each of the several figures are identified by the same reference numerals or by reference numerals having the same last three digits.

DESCRIPTION OF THE PREFERRED EMBODIMENTS

The suturing instrument of the present invention can be utilized to suture any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen.

A suturing instrument 10 in accordance with the present invention, as illustrated in FIGS. 1–7, includes a hub or housing 12, a handle 14 coupled with a proximal end of the housing, an outer tubular member 16 extending distally from the housing, an inner tubular member 18 disposed in the outer tubular member with a small radial clearance to define an annular space 20 therebetween, and a needle holder 22 movably disposed in the annular space between the inner tubular member and the outer tubular member.

Figure 1:
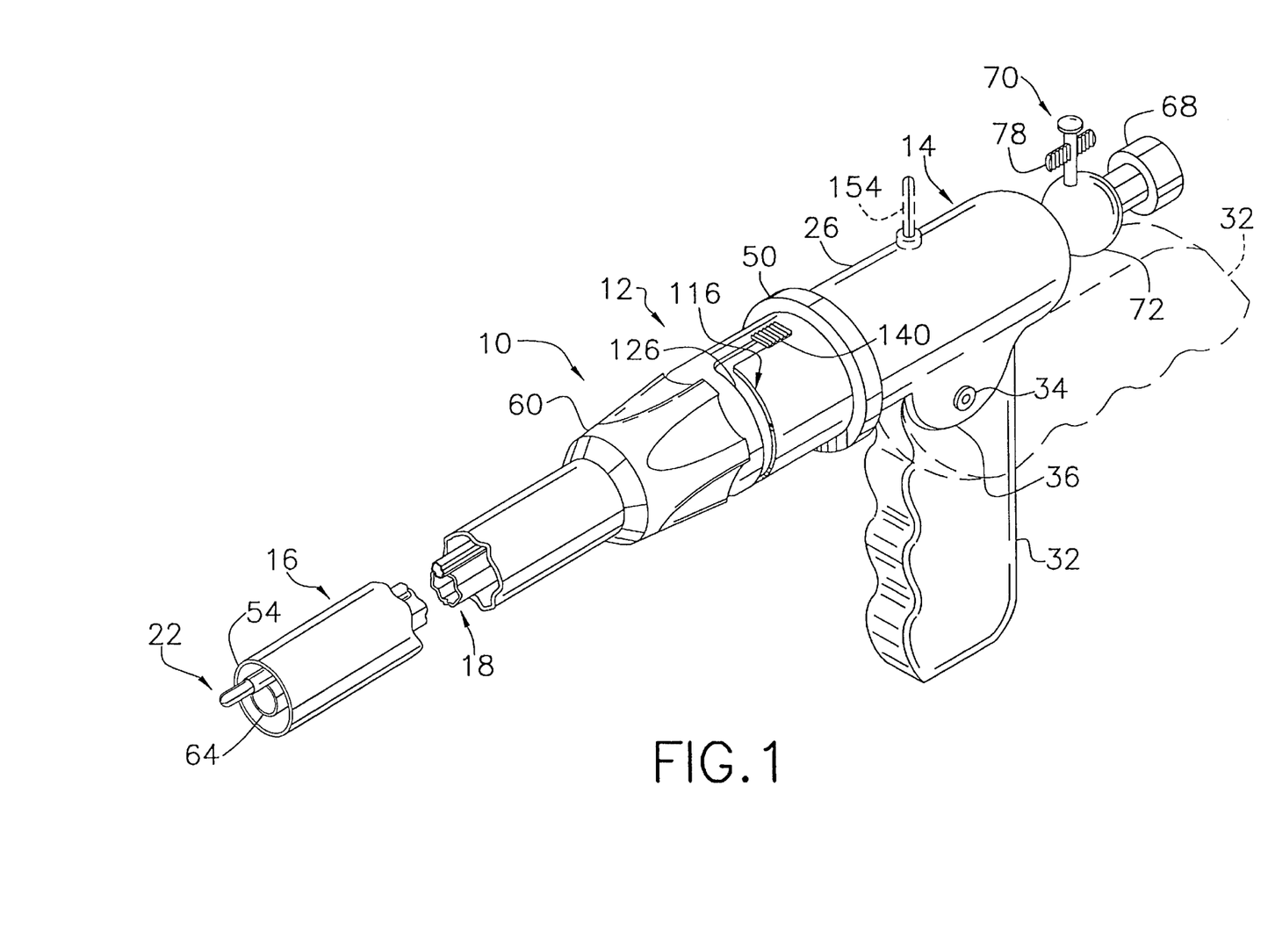
FIG. 1 is a perspective view, broken longitudinally, of a suturing instrument according to the present invention.
Figure 2:
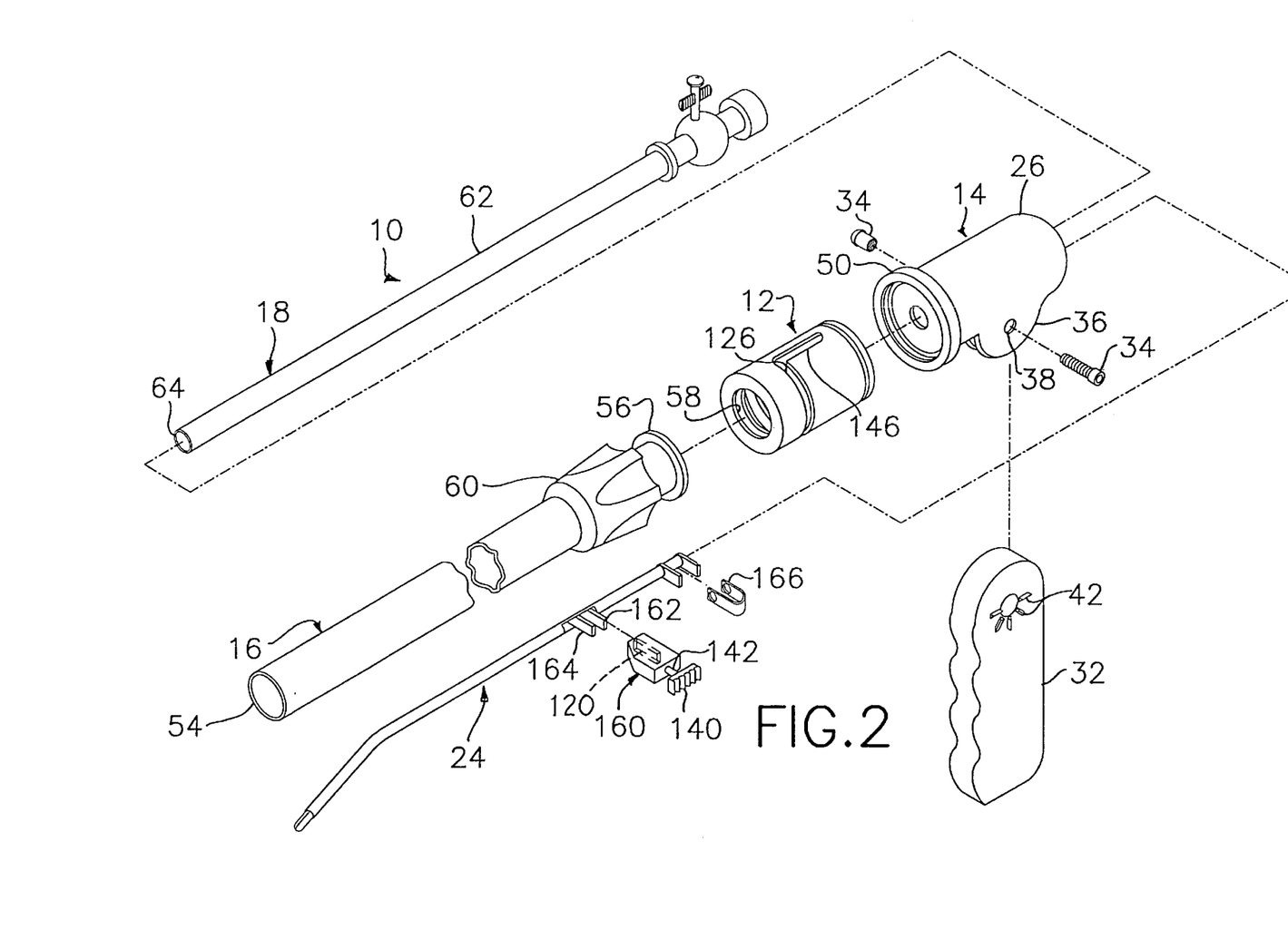
FIG. 2 is an exploded perspective view of the suturing instrument of FIG. 1.

Handle 14 includes a hollow cylindrical portion or housing 26 with longitudinally spaced front and rear walls 28 and 30 oriented perpendicular to a longitudinal axis of the inner tubular member and a pistol grip 32 pivotally mounted on a bolt or pin 34 secured between spaced, parallel flanges 36 extending outwardly from the handle housing. As best seen in FIG. 2, opposite sides of the pistol grip adjacent bolt hole 38 are each provided with one or more radial ribs or ridges 40 which extend outwardly from the pistol grip to fit within cooperatively formed grooves 42 on the inside of flanges 36 to form a detent structure allowing the pistol grip to be locked in a desired position with a ratcheting-like movement when the bolt or pin is tightened. For example, in FIG. 1, the pistol grip is shown extending transversely from the housing at an acute angle relative to the proximal direction. It will be appreciated, however, that the pistol grip can be pivoted in a counterclockwise direction (shown by broken lines in FIG. 1) or in a clockwise direction (not shown) dependent upon the procedure to be performed and the preference of the user. It is also possible to use the instrument housing as a handle, in which case a separate handle need not be attached.

Figure 3:
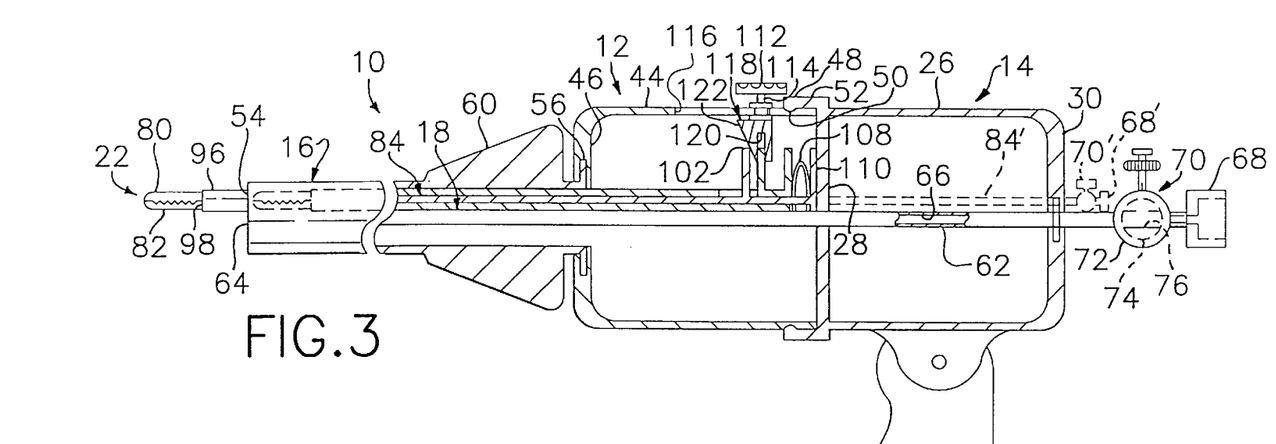
FIGS. 3 and 4 are a side view, partly in section, and a front view, respectively, of the suturing instrument of FIG. 1 with the needle holder in an undeployed position.

Referring to FIGS. 2 and 3, housing 12 includes a hollow, cylindrical portion or side wall 44 with an open proximal end and a front wall 46 at a distal end extending perpendicular to the longitudinal axis of the outer tubular member. A groove 48 is formed about the circumference of the housing side wall adjacent the open proximal end. A cylindrical skirt or rim 50 protrudes from handle 14 in a distal direction to fit telescopically around the proximal end of housing 12 and terminates at a flange 52 which extends radially inward from the skirt or rim to be received within groove 48 to permit rotation of the handle relative to the housing. Flange 52 fits frictionally within groove 48 so that the handle can be locked in any position relative to the housing. The instrument handle and housing can be made of any substantially rigid medical grade material but are preferably formed of a plastic material of relatively high durometer to reduce weight while offering structural support for the distally extending members of the instrument.

Outer tubular member 16 is open at both ends and extends distally from housing 12 through an opening in front wall 46 of the housing. Distal end 54 of the outer tubular member can be blunt as shown, tapered, beveled, slotted or chamfered as desired or have any other distal configuration suitable for a particular procedure. Preferably, outer tubular member 16 is made of a substantially cylindrical length of a substantially rigid material, such as stainless steel or some other medically acceptable plastic or metal material. The outer tubular member terminates proximally at an outwardly extending flange 56 fixedly mounted within a recess 58 formed in the front wall of the housing such that the outer tubular member rotates with the housing. A generally frustoconical collar 60 of decreasing diameter in the distal direction extends outwardly from the outer tubular member adjacent the front wall of the housing and is configured with longitudinal fluting to facilitate manual rotation of the handle relative to the housing.

Inner tubular member 18 includes an elongate cylindrical portion 62 of hollow configuration disposed coaxially within outer tubular member 16 and having an outer diameter somewhat smaller than the inner diameter of the outer tubular member to define an annular space 20 therebetween having a radius of curvature less than the radius of curvature of the suture needle to be used. The hollow cylindrical portion 62 of the inner tubular member extends proximally from a distal end 64 aligned with distal end 54 of the outer tubular member through rear wall 30 of the handle housing to define a longitudinal operating channel or passage 66 through the instrument. The inner tubular member terminates at a coupling 68, for example a Luer lock, for connection with sources of fluid or suction, operating units, medical instruments and accessories, with a valve 70 being disposed between the hollow cylindrical portion of the inner tubular member and the coupling, the valve including a hollow spherical valve housing 72 preferably formed integrally with the inner tubular member from a substantially rigid medically acceptable plastic or metal material, and a spherical valve member 74 with a cylindrical aperture opening 76 formed therethrough rotatably disposed within the valve housing and connected with a knob 78.

Needle holder 22 includes a pair of cooperating needle holding members, defining a needle holding portion, mounted by the handle for rotation along an arcuate path about a longitudinal axis of the instrument, the needle holding members further being movable relative to one another to selectively grasp and release a suture needle during suturing procedures.

Needle holding members 80 and 82 of needle holder 22 are shown as a pair of pivotably opposed jaws in FIGS. 1–12 but can have other configurations for grasping and releasing a suture needle as well as for performing other functions during a surgical procedure. Jaws 80 and 82 are preferably formed at the distal end of an elongate rod 84 of solid cross-section as an integral one-piece unit; however, it will be appreciated that the jaws can be formed separately for attachment to the rod and that the rod can be of hollow, tubular configuration to define an additional operating channel as shown, for example, by broken lines at 84' in FIG. 3 with a valve 70' and a coupling 68'. The jaws of the needle holder are biased apart toward an open position, shown at the top of FIG. 7, where inner needle holding or grasping surfaces 86 and 88 of the jaws are angularly spaced from one another. Opposed inner surfaces 86 and 88 of the jaws are shown with a plurality of longitudinally spaced teeth or ribs 90 oriented perpendicular to the longitudinal axis of the rod to securely hold a suture needle, tissue or other objects therebetween during a surgical procedure. In addition, inner surfaces 86 and 88 are oriented to permit a suture needle having a radius of curvature to be held between the jaws of the needle holder such that the needle extends from the jaws along an arcuate path coaxial with the central longitudinal axis of the inner tubular member. Rod 84 includes a proximal portion 92 of generally straight configuration disposed within the annular space 20 between inner and outer tubular members, and a distal portion 94 with a predetermined deployed shape or condition where the distal arm portion bends outwardly at an angle relative to the longitudinal axis of the proximal portion of the rod, the distal portion assuming the deployed shape or condition when the needle holder is in an extended position with the distal portion protruding distally beyond the distal end 54 of the outer tubular member as shown, for example, by solid lines in FIG. 5. The length and angular deflection of the distal portion of the rod are such that at least portions of jaws 80 and 82 are spaced laterally outward of a peripheral edge or diameter of the outer tubular member when the distal portion is in the deployed condition. Preferably, the distance between the axis of rotation of the needle holder and the position of needle holding surfaces 86 and 88 is approximately equal to the radius of curvature of the suture needle to be used so that the suture needle can be held between the needle holding surfaces and driven through anatomical tissue along an arcuate path having a radius of curvature commensurate with the needle radius of curvature to minimize tissue trauma. The rod is preferably formed of an elastic material, such as a spring steel, having elastic properties allowing the distal portion to bend inwardly, in a lateral direction relative to the longitudinal axis of the rod, when the rod is moved proximally relative to the outer tubular member from the extended position shown in FIGS. 5 and 6 to the retracted position shown in FIGS. 3 and 4. In the retracted position, a sufficient amount of the distal portion of the rod is disposed within the outer tubular member to cause the distal portion to assume an undeployed shape or condition where the jaws do not protrude beyond the periphery or diameter of the outer tubular member. If desired, however, the instrument can be modified to permit complete retraction of the needle holder to positions where the jaws are proximally spaced from the distal end of the outer tubular member as shown by broken lines in FIG. 3.

A flexible outer member or sleeve 96 of tubular configuration fits telescopically around rod 84 and is axially movable along the length of the rod between a retracted position where a distal end 98 of the flexible sleeve is proximally spaced from the jaws and an extended position where the distal end of the flexible outer member slides over the jaws. The flexibility of sleeve 96 is such that the sleeve will preferably conform to the shape of the rod even when in the outwardly bent, deployed position. A relatively rigid flange or tongue 100 extends laterally outward from flexible sleeve 96 within the instrument housing, and a similar flange or tongue 102 extends outwardly from rod 84 through a slot 104 formed in the sleeve to be disposed distally of the sleeve tongue 100. Flexible sleeve 96 terminates proximally at a second flange 106, and a bias member 108, for example a leaf spring of generally U-shaped configuration, is held in compression between sleeve proximal flange 106 and a flange 110 mounted on the rod proximally of the sleeve proximal flange to bias tongues 100 and 102 together so that the distal end 98 of the flexible sleeve is biased to move distally relative to the rod to an extended position where the distal end of the sleeve slides over jaws 80 and 82, causing the jaws to close.

Figures 4, 6, 7, 12:
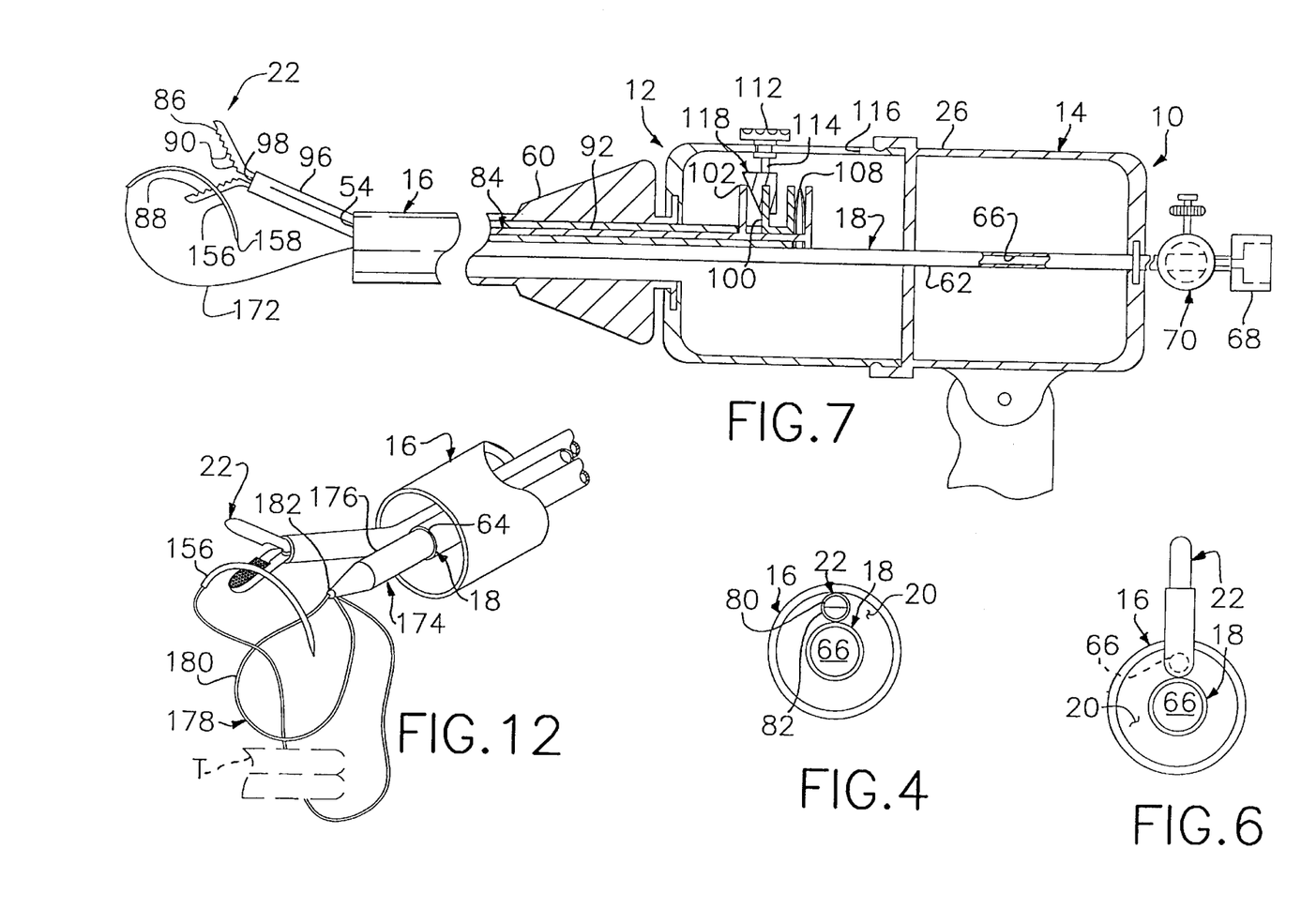
FIGS. 5 and 6 are a side view, partly in section, and a front view, respectively, of the suturing instrument of FIG. 1 with the needle holder in a deployed position.
FIG. 7 is a side view, partly in section, illustrating operation of needle holding members of the needle holder.
FIG. 12 is a fragmentary perspective view of the suturing instrument according to the present invention with a ligating device inserted therethrough.
Figure 5:
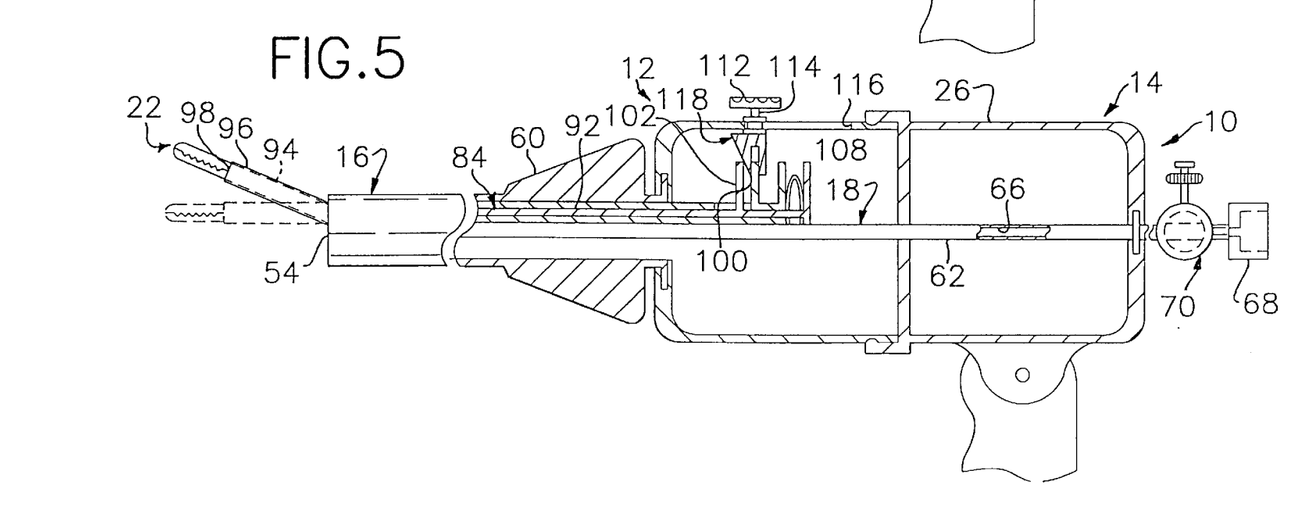

A push button 112 is disposed externally of the instrument housing and is mounted on a plunger or post 114 which extends from the button through a slot 116 in the housing to a wedge 118 disposed within the housing. The wedge defines a slot or groove 120 for receiving tongue 100 and has a width of decreasing dimension in a laterally inward direction to define an angled distal face or cam surface 122 which acts on tongue 102 to spread tongues 100 and 102 apart when the button is in a depressed position or condition, as shown at the top of FIG. 7, and to maintain contact with tongue 100 when in an elevated or non-depressed position or condition, as shown in FIGS. 3 and 5, such that movement of the push button along the slot will cause the wedge to impart movement to the needle holder as a whole. Push button 112 is preferably of a known type which will alternatingly extend the plunger inwardly and retract the plunger outwardly in response to repeated depression. In addition, it is preferred that a portion of the push button mechanism slide frictionally within the slot 116 so that, once the push button has been moved to a desired position along the slot, the push button will not move until forced deliberately by the user. As best seen in FIGS. 1 and 2, slot 116 includes a longitudinal portion 124 oriented parallel to a longitudinal axis of the housing and a transverse portion 126 extending perpendicularly from a distal end of the longitudinal slot portion in a clockwise direction looking proximally, the transverse portion extending about a third of the way around the circumference of the housing. Slot 116 may also include a proximal transverse portion as shown, for example, by broken lines in FIG. 1 at 150, to permit arcuate rotation of the needle holder in an axially retracted position.

An electrical connector can optionally be mounted on the handle 14, as shown by broken lines at 154 in FIG. 1, or at any other suitable location on the instrument including, but not limited to, the side of instrument housing 12 or the proximal end of inner tubular member 18 adjacent valve 70, to connect electrically conductive elements of the instrument with a source of electricity for performing unipolar or bipolar procedures such as electric coagulation, for example using one or both of the jaws of the needle holder as conductive elements. In addition, an interior surface of the operating channel 66 can be coated with an electrical and/or thermal insulating layer to permit safe insertion of electrical, thermal and/or other types of energy transmitting devices through the operating channel.

In use, instrument 10 is grasped using pistol grip 32 and, in the case of an endoscopic procedure, the instrument is guided to the operative site by a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. Visualization of the endoscopic procedure can be accomplished using a conventional endoscope incorporated into the instrument, for example within the longitudinal operating channel 66 defined by tubular shaft 62, or separately positioned within the anatomical cavity through a second portal sleeve located at another puncture site.

Prior to insertion, instrument 10 is preferably in the position shown in FIGS. 1 and 3. More specifically, needle holder or driver 22 is preferably initially positioned at an axially retracted position within annular space 20, for example by sliding push button 112 counterclockwise, looking proximally, within transverse slot portion 126 until post 114 is disposed within longitudinal slot portion 124 and then sliding the push button proximally along the longitudinal slot portion until the post abuts a proximal end of slot 116. Needle holder 22 should then be in the axially retracted position with jaws spaced laterally inward of the peripheral edge of the outer tubular member in an undeployed condition so as not to snag or catch on structure within the portal sleeve or valve housing during insertion. To this end, push button 112 is preferably initially disposed in the elevated position shown in FIG. 3 so that the needle holder will be in the closed or grasping position with inner grasping surfaces of the jaws close together or abutting one another. Alternatively, or in addition to the above, a sheath (not shown) can be telescopically fitted around the elongate tubular member or shaft in a manner to be movable axially or longitudinally between a retracted position spaced proximally of the end effectors and an extended position protruding distally from the shaft to cover and protect the end effectors.

After insertion, needle holder 22 is preferably moved distally relative to outer tubular member 16 from the retracted, undeployed position shown in FIGS. 3 and 4 to the extended, deployed position shown in FIGS. 5 and 6 by sliding button 112 distally along longitudinal slot portion 124. As the needle holder is advanced longitudinally, a distal portion of the needle holder is no longer laterally restrained within the outer tubular member and will thus bend outwardly, away from the longitudinal axis of the outer tubular member, toward a deployed position where the jaws of the needle holder are spaced laterally outward of the peripheral edge of the outer tubular member.

Figures 8, 9, 10, 11:
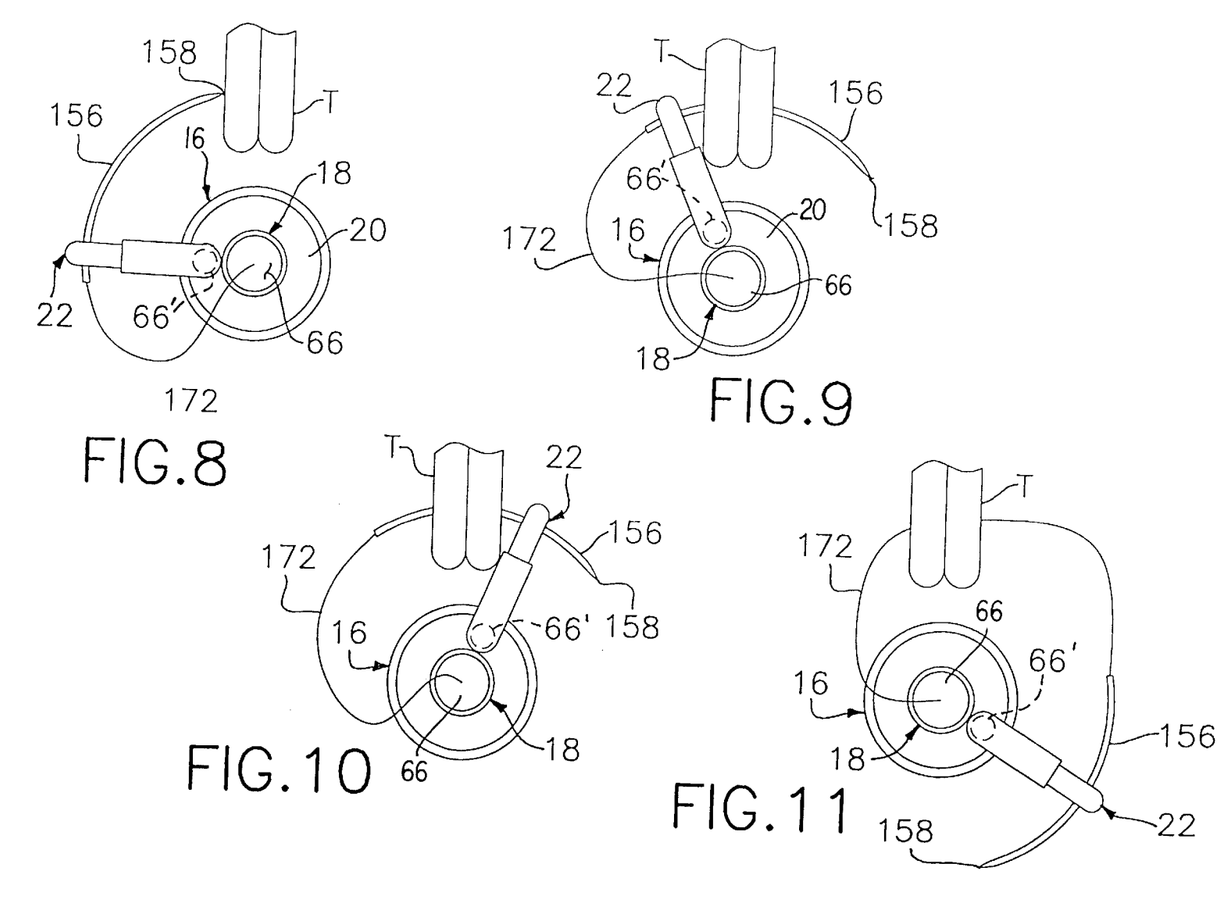
FIGS. 8–11 are front views of the suturing instrument of FIG. 1 illustrating use of the instrument for suturing anatomical tissue with a curved suture needle.

A curved suture needle 156, preferably having a radius of curvature commensurate with the distance between the axis of rotation of the needle holder and the deployed position of the needle holder jaws, is positioned in needle holder 22 by moving jaws 80 and 82 apart from the closed position shown in FIG. 5 to the open position shown in FIG. 7, placing the body of the suture needle in the space between the jaws, and moving the jaws toward the closed position until grasping surfaces 86 and 88 abut the suture needle to hold it firmly in place. Jaws 80 and 82 are moved to the open position by depressing the push button 112 to cause the wedge 118 to spread tongues 100 and 102 apart against the influence of bias member 108, as shown in FIG. 7, such that distal end 98 of the sleeve 96 is moved proximally relative to the jaws. The body of needle 156 is then placed between grasping surfaces 86 and 88 of the needle driver with the body of the needle being oriented transverse to the longitudinal axis of the distal portion of the needle holder and, preferably, coaxial with the axis of rotation of the needle holder. With needle 156 positioned within jaws 80 and 82 of needle holder 22, push button 112 is depressed to cause the wedged-shaped terminal end 118 to elevate or move away from tongues 100 and 102 so that the tongues can move together under the influence of bias member 108. Movement of tongue 100 towards tongue 102 causes distal end 98 of sleeve 96 to move distally relative to rod 84 and into camming contact with jaws 80 and 82, causing the jaws to move toward one another and into gripping contact with the body of needle 156 as shown in FIG. 8. Needle 156 is thus held securely between jaws 80 and 82 and will move with needle holder 22 during the suturing procedure.

Referring now to FIG. 8, tip 158 of needle 156 is positioned adjacent anatomical tissue T with a length of filamentous suture material 172 being shown attached to the proximal end of the needle for purposes of illustration only. The needle is driven through tissue T either by rotating the instrument in a clockwise direction, looking proximally, or by rotating knob 112 in a clockwise direction, looking proximally, along transverse slot portion 126 until post 114 abuts the opposite terminal end of the transverse slot portion or needle holder 22 abuts the tissue being sutured. Tip 158 of needle 156 is thus caused to penetrate through the anatomical tissue T along an arcuate path having a radius of curvature approximately equal to or commensurate with the radius of curvature of the needle until the tip is disposed at a location spaced clockwise from the tissue as shown in FIG. 9. During rotation of needle holder 22, it will be appreciated that wedge 118 maintains the radial or outward orientation of tongues 100 and 102 while preventing the tongues from becoming spread apart, thus maintaining grasping pressure on the suture needle.

Needle 156 is then released from needle holder 22 by moving jaws 80 and 82 to the open position in the manner described above. The suture needle 156 is thus released from the jaws of needle holder 22 but is held in place within tissue T due to friction and the tendency of the tissue to resist further penetration. After releasing the suture needle on one side of the tissue, the needle holder is repositioned to receive the tip of the suture needle on the other side of the tissue, for example by rotating the instrument in a counterclockwise direction, looking proximally, or by rotating knob 112 in a counterclockwise direction, looking proximally, along transverse slot portion 126 until jaws 80 and 82 of the needle holder are disposed on opposite sides of the needle body as shown in FIG. 10. If the instrument is held relatively stationary as knob 112 is used, the needle holder can be accurately repositioned with minimum adjustment by the user, particularly when the arcuate movement of the needle holding members is predefined to correspond to or be commensurate with the needle radius of curvature.

With needle 156 positioned within jaws 80 and 82 of needle driver 22, push button 112 is depressed to cause the jaws to move toward one another and into gripping contact with the body of needle 156. The suture needle 156 is then pulled through the tissue as shown in FIG. 11, for example by rotating the instrument and the needle holder as a unit in the clockwise direction, looking proximally, or by rotating button 112 in the clockwise direction, looking proximally, to cause the needle holder jaws to move along an arcuate path having a radius of curvature commensurate with the needle radius of curvature. Suture needle 156 is thus pulled through the anatomical tissue with the length of suture material 172. At this point, the length of suture material can be knotted to form a single stitch or another stitch can be made by driving the suture needle through the anatomical tissue at a second site or location using the needle holder. At some point, the suture needle 156 may need to be advanced circumferentially in the clockwise direction in order for the tip 158 to protrude sufficiently from the needle holder for additional stitches to be formed. Such repositioning can, for example, be accomplished by grasping the proximal end of the needle with a separate needle holding instrument and releasing the needle holding members of the needle holder to allow manipulation of the needle to a position in the needle holder wherein the tip of the needle protrudes sufficiently to pass through the anatomical tissue.

At any point during the surgical procedure, operating channel 66 of the suturing instrument can be used for irrigation or aspiration of the surgical site and can serve as a space for holding the suture material or as a portal for the introduction of other medical instruments and devices such as, for example, forceps, cutting members, needles, endoscopes as well as other needle holders. Knotting elements can also be introduced at the operative site via the operating channel for use in lieu of or in addition to traditional knotting techniques during the suturing procedure. Some examples of suitable knotting elements for this purpose are described in pending application Ser. No. 08/366,285, filed Dec. 29, 1994; Ser. No. 08/377,723, filed Jan. 25, 1995; Ser. No. 08/401,002, filed Mar. 9, 1995; and Ser. No. 08/585,875, filed Jan. 16, 1996; the disclosures of which are incorporated herein by reference.

FIG. 12 illustrates a further use of operating channel 66 wherein a ligating device 174 is advanced distally through the channel to assist in tying a suture. The device 174 is of the conventional ENDOLOOP-type and includes an elongate tubular pusher 176 and a length of filamentous ligature material 178 extending through the pusher to define a loop 180 with a knotting element 182 in the form of a pretied knot at the distal end of the pusher. For purposes of illustration, a free end of the ligature material is shown attached to the proximal end of suture needle 156 so that, after the suture needle has been pulled through anatomical tissue with the ligature material, the needle can be passed through the loop and the loop can be tightened to control the tension of the suture.

In addition to the main operating channel 66, an auxiliary operating channel can be defined through the needle holder as shown by broken lines at 66' in FIGS. 8–11 to provide access to the operative site from outside the anatomical cavity. The auxiliary operating channel can terminate distally at an opening adjacent the jaws of the needle holder or at an opening defined at the bend connecting straight and angled portions of the needle holder.

Figures 13, 14, 15, 16, 17, 20, 24, 25:
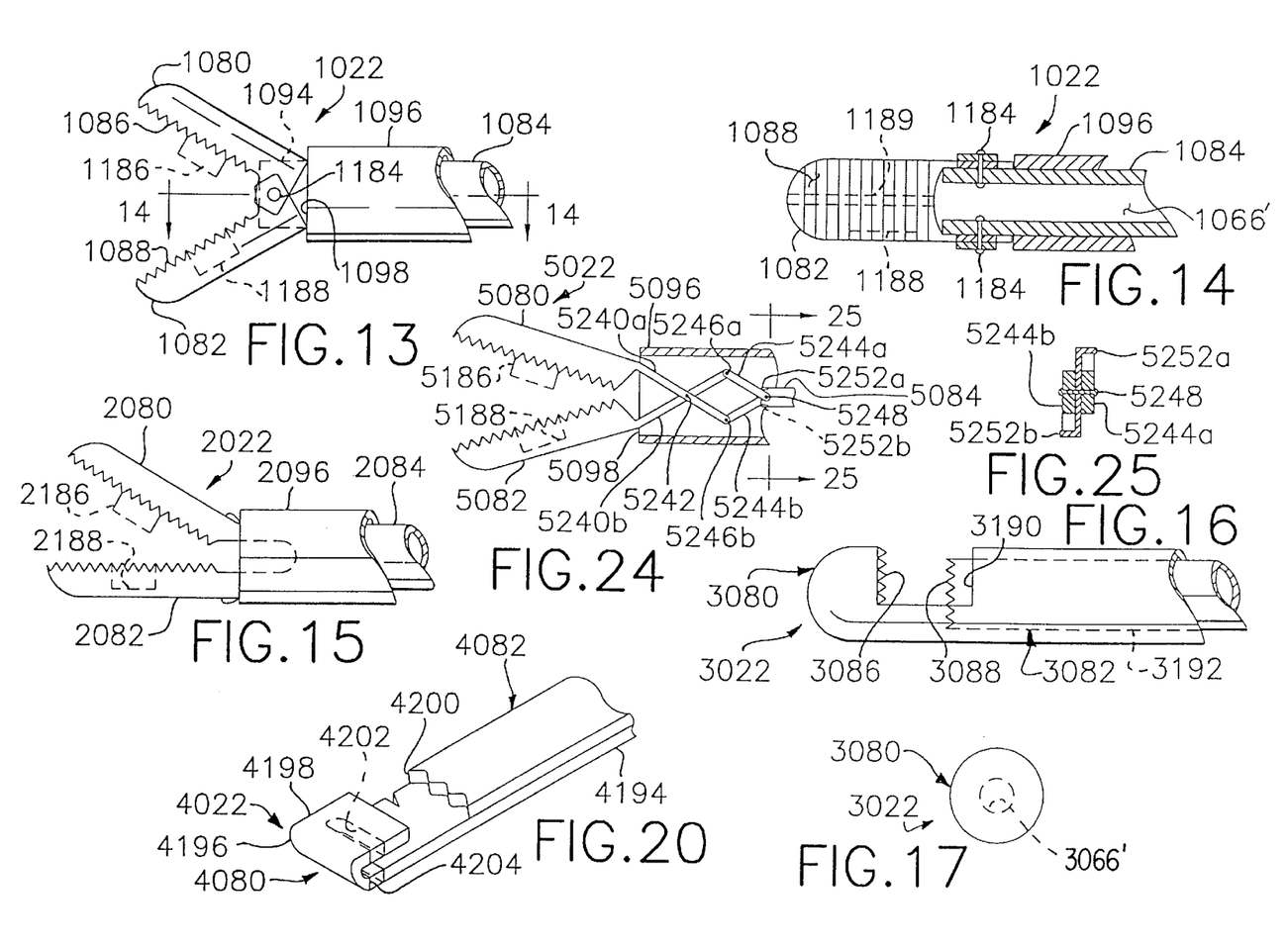
FIG. 13 is a fragmentary side view of a modified needle holder for use with the suturing instrument according to the present invention.
FIG. 14 is a cross-sectional view of the modified needle holder taken through line 14—14 in FIG. 13.
FIG. 15 is a fragmentary side view of another modification of a needle holder for use with the suturing instrument according to the present invention.
FIGS. 16 and 17 are a fragmentary side view and a front view, respectively, of another modified needle holder for use with the suturing instrument according to the present invention.
FIG. 20 is a fragmentary perspective view of still another modification of a needle holder for use with the suturing instrument according to the present invention.
FIG. 24 is a fragmentary side view, partly in section, of yet another modification of a needle holder for use with a suturing instrument according to the present invention.
FIG. 25 is a cross-sectional view of the needle holder shown in FIG. 24 taken through line 25—25.

FIGS. 13 and 14 show a modification of a needle holder 1022 for use with the suturing instrument according to the present invention wherein the modified needle holder 1022 includes a pair of jaws 1080 and 1082 pivotably mounted on a pair of pins 1184 secured to diametrically opposed sides of a hollow tubular rod or sleeve 1084 telescopically fitted within an outer tubular sleeve 1096, the tubular rod defining an auxiliary operating channel 1066' providing access to the operative site from outside the anatomical cavity. Jaws 1080 and 1082 are biased apart toward the open position shown in FIG. 13, for example using a torsion spring (not shown) coiled around one of the pins and connected between the jaws or a pair of spring members (not shown) held in compression between each jaw and the hollow tubular rod, and the jaws are movable inwardly toward one another against the spring bias in response to distal movement of outer tubular sleeve 1096 against the rear or back edges of the jaws.

Any of the needle holding members described herein can carry a biopsy box or a cutting member such as the blade shown by broken lines at 1186 in FIG. 13. Blade 1186 is oriented perpendicular to inner surface 1086 of the upper jaw 1080 and extends inwardly from the inner surface to fit within a cooperatively configured pocket or recess 1188 formed in lower jaw 1082 when the jaws are closed together. An elongate groove or recess with an open proximal end can be formed along an inner surface of one or both of the jaws, for example as shown by broken lines at 1189 in FIG. 14, to permit a cutting member, such as a blade, to slide between the jaws when closed. Examples of other cutting members which can be used are shown and described in U.S. patent application Ser. No. 08/612,634, filed Mar. 4, 1996, and Ser. No. 08/376,186, filed Jan. 20, 1995, the disclosures of which are incorporated herein by reference.

The modified needle holder 2022 shown in FIG. 15 is similar to the needle holders shown in FIGS. 1–11 but with a hollow, tubular rod or sleeve 2084 of generally cylindrical configuration defining an operating channel 2066' along the length of the needle holder and a pair of jaws 2080 and 2082 formed integrally with the hollow tubular rod as a one-piece unit. The lower jaw 2082 in FIG. 20 is of fixed configuration and extends in parallel with a longitudinal axis of the hollow tubular rod while the upper jaw 2080 is pivotably movable between an open position extending outwardly from the tubular rod longitudinal axis at an angle and a closed position abutting the lower jaw. If desired, the fixed jaw can be formed integrally with the tubular rod and the movable jaw can be pivotably mounted on one or more pins as shown, for example, in FIGS. 13 and 14.

Yet another modified needle holder is shown in FIGS. 16 and 17 at 3022 and includes a first needle holding member in the form of an outer tubular sleeve 3096 with a lateral cut-out or window 3190 having a grasping surface 3086 formed along a proximal-facing peripheral edge of the window and a second needle holding member in the form of an inner tubular sleeve 3192 fitted telescopically within the outer tubular sleeve and having a grasping surface 3088 formed along a distal peripheral edge of the inner sleeve to operate cooperatively with the grasping surface of the window to hold a suture needle or other objects within the window while permitting access to the operative site via the channel defined by the inner tubular sleeve.

Figure 18:
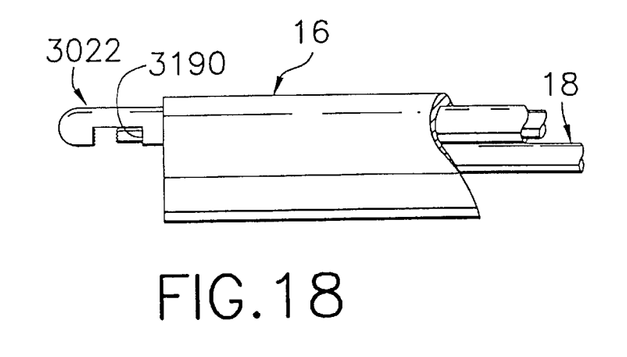
FIG. 18 is a fragmentary side view of the distal end of a suturing instrument according to the present invention with a modified needle holder as shown in FIG. 16 oriented to face inwardly.
Figure 19:
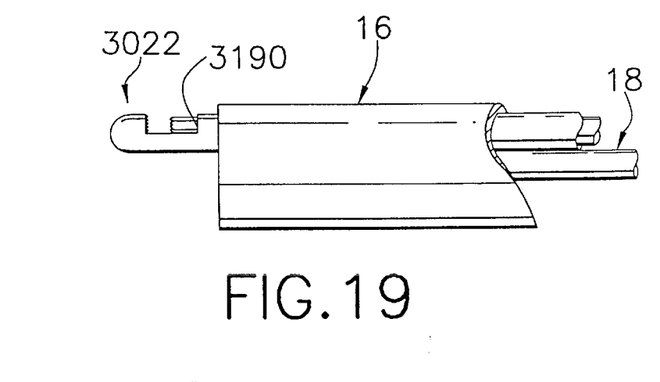
FIG. 19 is a fragmentary side view of the distal end of a suturing instrument according to the present invention with a modified needle holder as shown in FIG. 16 oriented to face outwardly.

The window 3190 in the outer tubular sleeve 3096 of the modified needle holder 3022 can be oriented to face any suitable direction relative to the central longitudinal axis of the outer tubular member of the suturing instrument dependent upon the shape of the suture needle or procedural use. For example, in FIG. 18, a needle holder 3022 is shown oriented such that window 3190 faces inwardly, toward the central longitudinal axis of the suturing instrument. By directing the window inwardly, the process of loading a suture needle into the needle holder from the central operating channel 66 can be simplified. In FIG. 19, on the other hand, the needle holder 3022 is oriented such that window 3190 faces outwardly, away from the central longitudinal axis of the suturing instrument.

FIG. 20 shows still another modification of a needle holder for use with the suturing instrument according to the present invention wherein the modified needle holder 4022 includes a first needle holding member 4080 in the form of a hook and a second needle holding member 4082 in the form of a keeper movable relative to the hook to capture and release a suture needle placed within the hook. The needle holding members are preferably formed of flat strips of a medically acceptable material, such as stainless steel, configured to lay flat against one another to permit relative sliding movement of the needle holding members. The first needle holding member 4080 includes an elongate portion or leg 4194 extending distally from within the instrument housing to a bend 4196 where the first needle holding member folds inwardly upon itself to form a short leg 4198 parallel to the elongate portion or leg of the needle holding member thereby defining a hook with a proximal-facing mouth having a gap width suitable for receiving the shaft or body of a suture needle. The second needle holding member 4082 is slidingly disposed along the first needle holding member 4080 and includes a distal end 4200 configured to fit within the mouth of the hook as a keeper, the distal end of the second needle holding member being shown with an optional scalloped edge having one or more curved recesses. The first or second needle holding member may also be formed with a cutting member such as a blade or a notch of generally V-shaped configuration defined along an edge of the needle holding member and having one or more sharp edges to cut lengths of suture material received therein under pressure. The first needle holding member is also shown with optional slots or openings 4202 and 4204 formed on opposite sides of the hook to permit straight or slightly curved suture needles to be placed perpendicularly through short and long legs of the hook so as to be oriented radially relative to the longitudinal axis of the inner tubular member. The slotted openings extend transversely, relative to a longitudinal axis of the needle holder, from respective open ends disposed along a lateral or longitudinal edge of the first needle holding member to generally centrally located terminal ends of rounded or semicircular configuration with a size to receive the body or shank of a suture needle extending transversely through legs of the hook. As mentioned above, the scalloped edge at the distal end of the second needle holding member or keeper 4082 is configured with laterally spaced recesses, one of which is preferably aligned with the terminal portion or end of the slotted openings to cradle a needle positioned within the openings in a manner to secure the needle during laterally inward and outward suturing procedures performed as described in patent application Ser. No. 08/758,648, filed Nov. 27, 1996, the disclosure of which is incorporated herein by reference.

Figures 21, 22, 23:
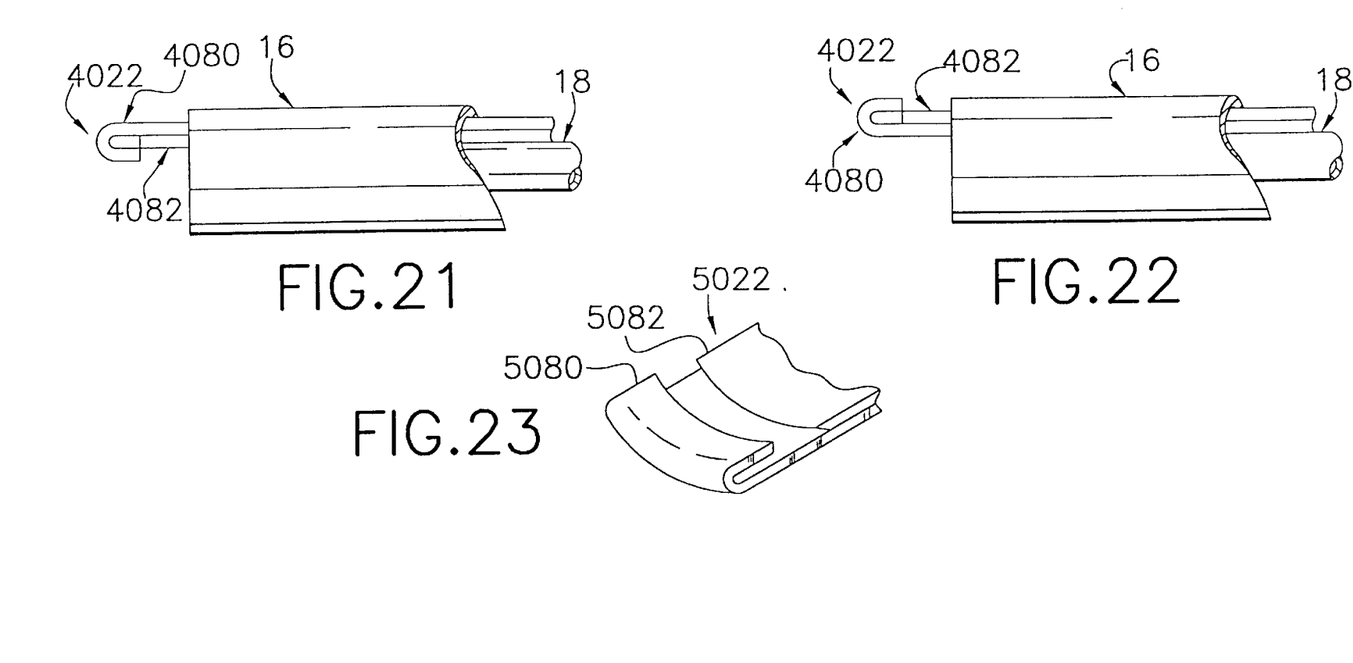
FIG. 21 is a fragmentary side view of the distal end of a suturing instrument according to the present invention with a modified needle holder as shown in FIG. 20 oriented to face inwardly.
FIG. 22 is a fragmentary side view of the distal end of a suturing instrument according to the present invention with a modified needle holder as shown in FIG. 20 oriented to face outwardly.
FIG. 23 is a fragmentary perspective view of yet another modification of a needle holder for use with the suturing instrument according to the present invention.

The hook-like needle holding member shown in FIG. 20 can be positioned within the annular space between the inner and outer tubular members of the suturing instrument such that the mouth of the hook formed at the distal end of the needle holding member opens inwardly as shown, for example, in FIG. 21, or outwardly, as shown in FIG. 22, dependent upon procedural use and the shape or radius of curvature of the suture needle. In the former case, the keeper is disposed between the hook-like member and the inner tubular member while in the latter case, the keeper is disposed between the hook-like member and the outer tubular member of the instrument.

Another modification of a needle holder is shown in FIG. 23 wherein the modified needle holder 5022 is similar to the needle holder shown in FIG. 20 but with greater circumferential width and having a curvature substantially commensurate with the radius of curvature of the suture needle to provide additional support for the body of the suture needle while still being able to slide conformally within the annular space between inner and outer tubular members 18 and 16.

Still another modification of a needle holder for use with the suturing instrument according to the present invention, as shown in FIGS. 24 and 25, includes a pair of jaws 6080 and 6082 extending distally from a pair of crossed arms 6240a and 6240b connected by a pivot 6242 located medially along the lengths of the arms. A pair of elongate linkages 6244a and 6244b extend inwardly from pivots 6246a and 6246b at respective proximal ends of the arms to a pivot 6248 connecting the linkages with an elongate rod 6084. Linkages 6244a and 6244b are disposed on opposite sides of the rod, with pivot 6248 extending through the linkages and the rod and with tabs or ears 6252 extending laterally outward from the rod in opposite directions to overhang the linkages as stops preventing the linkages from spreading outwardly beyond a predetermined position. Jaws 6080 and 6082 are moved relative to one another by moving the outer tubular member and rod relative to one another. The jaws are normally biased apart, for example by a torsion spring coiled around a pivot and connected between the jaws, and are closed by moving the outer tubular member distally relative to the jaws, for example by advancing the outer tubular member distally and/or pulling the rod in the proximal direction. In a preferred embodiment, the outer tubular member is biased distally relative to the jaws so that the jaws are normally in a closed position.

From the above, it will be appreciated that the suturing instrument according to the present invention permits suturing of anatomical tissue during endoscopic procedures without the need of having to use multiple needle holding instruments inserted through multiple puncture sites by inserting an elongate tubular member or shaft carrying an arcuately movable needle holder through a single puncture site. Preferably, the needle holder includes a distal portion movable between an undeployed, contracted or parked position spaced laterally inward of a peripheral edge of the elongate tubular member to facilitate insertion through a portal sleeve and a deployed, expanded or working position where at least part of the distal portion is spaced laterally outward of the peripheral edge of the elongate tubular member to permit use of suture needles having radii of curvature equal to or larger than a radial or lateral dimension of the elongate tubular member and to permit suturing of thicker tissue by increasing the working span or range of travel of the needle holder. The elongate tubular member is mounted by a handle or housing with controls for moving the needle holder axially and in an arcuate manner within the elongate tubular member. The needle holder includes needle holding members selectively operable to grasp and release a suture needle so that, when the needle holding members are operated to grasp the suture needle, the needle holder can be moved in a direction to drive the suture needle through anatomical tissue, and when the needle holding members are released, the needle holder can be accurately repositioned to pick-up the other end of the suture needle so that it can be pulled through the tissue. Movement of the needle holder can be accomplished by rotating the needle holder relative to the elongate shaft or by rotating the needle holder with the elongate shaft as a unit.

The needle holder of the suturing instrument can be configured to hold needles of any size or shape including, but not limited to, needles with straight or curved bodies or shanks. While the needle holder is shown disposed within an annular space or channel of generally circular configuration formed through the elongate tubular member or shaft, it will be appreciated that the arcuate channel can be of circular or non-circular curved configuration. A distal portion of the needle holder preferably extends laterally outward at an angle from a longitudinal axis of the elongate tubular member to carry the needle holding members so that, when the needle holders are moved arcuately within the periphery of the tubular member, the needle holding members are made to move arcuately along an arcuate path extending outwardly of the outer periphery of the tubular member. Any type of needle holder can be modified for use with the suturing instrument according to the present invention by configuring a distal portion of the needle holder to be normally bent outwardly at an angle relative to the proximal portion, including, but not limited to, any of the needle holders described in U.S. patent application Ser. No. 08/758, 648, filed Nov. 27, 1996, and Ser. Nos. 08/847,182, 08/847, 254, 08/847,253, 08/847,189, and 08/847,252, filed May 1, 1997, the disclosures of which are incorporated herein by reference. For example, any of the needle holders can include a transverse connecting member extending perpendicularly outward from a proximal portion of the needle holder to needle holding members laterally offset from the proximal portion.

One or more lengths of suture material can be attached to each suture needle at any desirable location along the body of tip of the needle including, but not limited to, the proximal end of the needle, intermediate or medial portions of the needle body, or locations adjacent the tip of the needle. It will also be appreciated that the suturing instrument according to the present invention can be used with suture needles having sharp or blunt tissue penetrating tips, and needles having tissue penetrating tips at opposite axial ends of a needle body.

The needle holding members of the needle holder shown and described herein are exemplary of the types of needle holding members that can be used according to the present invention. Accordingly, the needle holding members can have any suitable configuration for individually or cooperatively grasping needles to suture anatomical tissue including, but not limited to, jaw-like configurations wherein the needle holding members pivot, slide or otherwise move relative to one another to capture and release a needle. The needle holding members can be of straight, curved or angled configuration and can be provided with ribs, grooves, slots and/or holes along grasping surfaces to assure a positive grip. The needle holding members can also carry cutting members, such as slots with sharp edges or protruding blades, and can have opposed arcuate or concave portions for clamping tubular objects, such as organs, without compressing the objects, as well as portions configured to take a tissue sample for biopsy. When the needle holding members are carried at the distal end of one or more elongate components, for example a rod telescopically fitted within a tube, either component can include a distal portion of predetermined shape which, in an unrestrained condition, bends laterally outward at an angle relative to the longitudinal axis of the proximal portion of the needle holder component. Furthermore, components of a needle holder can be keyed or coupled to move together so that, for example, if one of the components is rotated the other component will be rotated as well.

The needle holder of the present invention can also be used as an end effector to perform lysis of adhesion, dissection, pickup and cutting, pickup and clipping, pickup and suturing with a suture needle, unipolar and bipolar electrosurgery, and numerous other procedures. Although the suturing instrument is shown and described herein as having a single needle holder, it will be appreciated that two or more needle holders can be used dependent upon the procedure to be performed and the preference of the user. When more than one needle holder is used, the additional needle holders can be straight or they can bend at a distal end like the needle holder described above. Also, the needle holder can be positioned at any location across the width or lateral extent of the shaft.

The needle holder of the present invention is preferably movably disposed about a tubular member defining one or more operating channels or passages through the instrument to permit various medical devices and instruments such as, for example, needles, blades, forceps, cauteries, endoscopes, illuminating devices and lengths of suture material to be introduced at the operative site without the need of having to remove the suturing instrument from the body. The tubular member defining the operating channel can have any configuration in transverse cross-section including, but not limited to, elliptical, polygonal and irregular or asymmetrical cross-sectional configurations. Also, all or part of the inner surface of the tubular member can be electrically insulated to permit passage of electrosurgical instruments therethrough. The valve and coupling shown at the proximal end of the tubular member are merely exemplary of the types of conventional valves and conventional couplings that can be used. Operating channels may also be defined along the length of the needle holder, if desired. The elongate tubular member or shaft can also have any configuration in exterior cross-section including, but not limited to, elliptical and rectangular cross-sections. The elongate tubular member can also include optical fibers disposed therein, or the elongate tubular member can be formed by the optical fibers themselves, for example by embedding or molding the optical fibers within a medically acceptable polymer matrix or by adhesively connecting the fibers together. When the elongate tubular member includes optical fibers, the operating channels can be formed by thin wall, tubular sleeves (as shown herein) or by voids or spaces defined between the optical fibers.

While the handle shown and described herein is configured primarily to be held by the user with one hand while operating the controls with another, it will be appreciated that the handle can also have configurations which permit one handed operation of the needle holder including, but not limited to, configurations wherein the handle includes pivoted legs with finger loops, one fixed and one pivoted leg with finger loops, a pistol grip with one or more movable triggers, and/or resilient U-shaped members. Moreover, the handle can be formed with the housing as an integral one-piece unit and can have any orientation relative to the longitudinal axis of the instrument including, for example, substantially transverse orientations wherein the handle extends transversely relative to the longitudinal axis of the instrument, substantially longitudinal orientations wherein the handle is oriented substantially parallel to or at a small angle relative to the longitudinal axis of the instrument, or rotatable configurations wherein the handle can be moved between transverse and longitudinal orientations as desired.

The mechanisms shown for controlling operation of the needle holding members of the needle holder and movement of the needle holder relative to the elongate tubular member or shaft are merely exemplary of the types of mechanisms that can be used to perform these functions. For example, in the case of slidable needle holding members, mechanisms including, but not limited to, controls in the form of push-buttons with wedge-shaped members for engaging flanges carried by each member, resilient U-shaped members with arms connected to each member, and triggers connected to the members via linkages or gears can be used to cause the needle holding members to move relative to one another. In the case of pivoted needle holding members or jaws, mechanisms such as tubular members movable relative to the jaws or linkages connecting one or both of the jaws with a trigger or the like at a proximal end of the instrument can be used to cause the needle holding member or jaws to move relative to one another. The needle holding members can be biased to a particular position, condition or state, such as an open state for receiving a suture needle or a closed state for grasping a suture needle, and can be provided with locking features to permit the user to maintain the members in a desired position.

Moving the needle holder arcuately relative to the elongate tubular member or shaft can be accomplished in any suitable manner, for example by connecting a knob at the proximal end of the needle holder and sliding the knob along a slot formed in the handle housing or by mounting the needle holder on geared components and moving the gears with a trigger or some other device. The particular length and curvature of the suture needles shown and described herein as well as any angular displacements of the needle holder shown and described herein are merely exemplary, and it will be appreciated that other needle lengths and angular displacements can be used. It will also be appreciated that the directions and angles of rotation of the needle holder described and shown herein are for purposes of illustration only and can be reversed and/or altered in magnitude dependent upon procedural use and the preferences of the user.

While the needle holders have been described herein as having a normally bent configuration which can be straightened by retracting the needle holders in a proximal direction relative to a tubular member so as to elastically deform the needle holders, it will be appreciated that the needle holders of the present invention can be moved between contracted and expanded positions using any suitable method including, but not limited to, methods utilizing linkages, gears, cables, movable stiffeners or inserts, shape memory materials, actuators or motors. Also, distal portions of the needle holders need not be straight as shown but can be curved or multiply angled, if desired.

The components of the suturing instrument of the present invention can be made of any suitable, medical grade materials to permit sterilization for reuse or disposal for single patient use. The components can be made of multiple parts of various configurations and materials to reduce cost. The handle and/or housing can have various valves, stop cocks and seals therein to control the flow of fluid and medical devices through the suturing instrument.

The features of the various embodiments described above can be combined in any manner desired dependent upon the operational requirements of the procedure to be performed and the complexity of the suturing instrument. It will also be appreciated that the suturing instrument of the present invention can be used to apply single or multiple stitches in open or endoscopic procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An instrument for suturing anatomical tissue with a suture needle, said instrument comprising
    an elongate tubular member having a proximal end and a distal end with a peripheral edge and extending along a longitudinal axis;
    a handle coupled to said proximal end of said elongate tubular members;
    a needle holder arm disposed offset relative to the longitudinal axis and extending from said distal end of said elongate tubular member, said needle holder arm being movable between an undeployed position where said needle holder arm is disposed laterally inward of said peripheral edge of said elongate tubular member and a deployed position where said needle holder arm is disposed laterally outward of said peripheral edge;
    said needle holder arm being coupled to said elongate tubular member for arcuate movement about the longitudinal axis of said elongate tubular member such that a distal end of said needle holder arm is caused to move along an arcuate path extending outwardly of said peripheral edge of said elongate tubular member.

2. An instrument as recited in claim 1 wherein said needle holder arm includes a needle holding portion having a pair of needle holding members having needle holding surfaces [radially spaced] on opposite sides of said arcuate path when said needle holder arm is in said deployed position.

3. An instrument as recited in claim 2 wherein said needle holding members include a pair of pivotally opposed jaws.

4. An instrument as recited in claim 3 wherein both of said jaws move relative to one another.

5. A suturing instrument as recited in claim 3 wherein a first of said jaws is fixed and a second of said jaws is movable relative to said first of said jaws.

6. An instrument as recited in claim 3 wherein said needle holder arm includes inner and outer telescoping members axially movable relative to one another, said jaws being mounted at the distal end of said inner telescoping member and being biased apart to an open position such that relative axial movement of said inner and outer telescoping members results in opening and closing of said jaws.

7. An instrument as recited in claim 2 wherein said needle holder arm includes a needle holding portion having a first needle holding member in the form of a hook and a second needle holding member having a distal end movable relative to said hook to grasp and release suture needles disposed within said hook.

8. An instrument as recited in claim 1 wherein said said needle holder arm is longitudinally movable relative to said elongate tubular member between an axially extended position where said needle holder arm extends outwardly in a lateral direction relative to a longitudinal axis of said elongate tubular member and a retracted position where said needle holder arm is moved inwardly toward said longitudinal axis.

9. An instrument as recited in claim 8 wherein said needle holder arm protrudes distally from said distal end of said tubular member in said extended position and is proximally spaced from said distal end of said tubular member in said retracted position.

10. An instrument as recited in claim 1 wherein said needle holder arm is coupled to a member extending at least partly through said elongate tubular member and extends laterally outward from said proximal member at an angle relative to a longitudinal axis of said proximal member when in a deployed position.

11. An instrument as recited in claim 10 wherein said needle holder arm is axially movable relative to said elongate tubular member between a retracted position where said needle holder arm is moved laterally inward toward said undeployed position and an extended position where said needle holder arm is permitted to spread laterally outward toward said deployed position.

12. An instrument as recited in claim 1 and further comprising an operating channel extending through said elongate tubular member.

13. An instrument as recited in claim 10 wherein an operating channel is defined by an inner tubular member disposed within said elongate tubular member with a small radial clearance to define an annular space therebetween, and said proximal member is movably disposed within said annular space.

14. An instrument as recited in claim 12 wherein said operating channel extends along the length of said instrument, and further comprising a coupling at a proximal end of said channel.

15. An instrument as recited in claim 12 wherein said operating channel extends along the length of said instrument, and further comprising a valve disposed along said longitudinal channel to control passage of fluids and instruments therethrough.

16. An instrument as recited in claim 1 wherein said arcuate path of said of said needle holder arm has a radius of curvature commensurate with the radius of curvature of the needle.

17. A method of suturing anatomical tissue using a length of suture material attached to a suture needle, said method comprising the steps of
    grasping the suture needle with a needle holder arm extending outwardly from a distal end of an elongate tubular member at an angle relative to a longitudinal axis of the elongate tabular member the needle holder arm being disposed offset relative to the longitudinal axis;
    driving the suture needle through the anatomical tissue in a first direction along an arcuate path having a radius of curvature substantially commensurate with the radius of curvature of the suture needle by moving the needle holder in a first direction along an arcuate path having a radius of curvature substantially commensurate with a radius of curvature of the suture needle so that the tip of the needle penetrates the anatomical tissue;
    releasing the suture needle from the needle holder arm;
    repositioning the needle holder arm to receive the tip of the suture needle by moving the needle holder arm in a second direction along an arcuate path having a radius of curvature substantially commensurate with the radius of curvature of the suture needle;
    regrasping the suture needle with the needle holder arm; and
    pulling the suture needle through the anatomical tissue by moving the needle holder arm in the first direction along an arcuate path having a radius of curvature substantially commensurate with the radius of curvature of the suture needle.

18. A method of suturing anatomical tissue as recited in claim 17 wherein said step of driving the suture needle through the anatomical tissue includes the step of rotating the elongate tubular member with the needle holder arm as a unit about a longitudinal axis of the elongate tubular member to drive the suture needle through the anatomical tissue.

19. A method of suturing anatomical tissue as recited in claim 18 wherein said step of driving the suture needle through the anatomical tissue includes the steps of maintaining the elongate tubular member in a substantially stationary position and moving the needle holder arm along an arcuate path about a longitudinal axis of the elongate tubular member in the direction of the tissue.

20. A method of suturing anatomical tissue as recited in claim 17 and further comprising, prior to said step of driving the suture needle through the tissue, the step of
causing the needle holder arm to move laterally outward from an undeployed position spaced inwardly of the peripheral edge of the elongate tubular member to a deployed position spaced outwardly of the peripheral edge of the elongate tubular member.

21. A method of suturing anatomical tissue as recited in claim 17 and further comprising, prior to said step of driving the suture needle through the tissue, the step of
causing the needle holder arm to move distally relative to the elongate tubular member from a retracted position within the elongate tubular member to an extended position protruding from the distal end of the elongate tubular member.

\* \* \* \* \*